(12) United States Patent
Hüttenbrink et al.

(10) Patent No.: US 10,022,534 B2
(45) Date of Patent: Jul. 17, 2018

(54) INSERTION SYSTEM FOR INSERTING IMPLANTABLE ELECTRODE CARRIER

(75) Inventors: Karl-Bernd Hüttenbrink, Dresden (DE); Daniel Sieber, Innsbruck (AT); Eckhard Schulz, Starnberg (DE); Martin Zimmerling, Patsch (AT); Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 585 days.

(21) Appl. No.: 13/380,360

(22) PCT Filed: Jun. 25, 2010

(86) PCT No.: PCT/US2010/039996
§ 371 (c)(1),
(2), (4) Date: Apr. 4, 2012

(87) PCT Pub. No.: WO2010/151768
PCT Pub. Date: Dec. 29, 2010

(65) Prior Publication Data
US 2012/0184804 A1    Jul. 19, 2012

Related U.S. Application Data

(60) Provisional application No. 61/220,630, filed on Jun. 26, 2009.

(51) Int. Cl.
*A61N 1/05*     (2006.01)

(52) U.S. Cl.
CPC .................................. *A61N 1/0541* (2013.01)

(58) Field of Classification Search
CPC ...... A61N 1/0541; A61B 17/29; A61B 17/30; A61B 17/28; A61B 17/2804;
(Continued)

(56) References Cited

U.S. PATENT DOCUMENTS 5,720,742 A * 2/1998 Zacharias .................... 606/1
5,792,199 A    8/1998 Fayram et al.
(Continued)

FOREIGN PATENT DOCUMENTS

EP    1145734 A2    10/2001
EP    1179969 A2    2/2002
(Continued)

OTHER PUBLICATIONS

International Searching Authority—International Search Report—International Application No. PCT/US2010/039996 dated Sep. 27, 2010, together with the Written Opinion of the International Searching Authority, 13 pages.

*Primary Examiner* — Jocelin Tanner
(74) *Attorney, Agent, or Firm* — Sunstein Kann Murphy & Timbers LLP (57) ABSTRACT

An insertion system for inserting an implantable electrode carrier includes an insertion instrument having a housing with a proximal end and a distal end, and a vibration generator coupled adjacent to the housing. The proximal end is configured to hold the implantable electrode carrier. The vibration generator is configured to generate vibrations in at least a portion of the electrode carrier.

34 Claims, 7 Drawing Sheets

(58) Field of Classification Search
CPC ............ A61B 17/2812; A61B 17/2909; A61B 2017/2804; A61B 2017/2808; A61B 2017/2901; A61B 2017/2926; A61B 2017/2947
USPC .................. 606/129, 205–211, 169; 604/22; 310/355, 14, 49.13, 15, 23, 30, 50, 179, 310/181, 183; 318/135, 400.37, 400.39
See application file for complete search history.

(56) References Cited

U.S. PATENT DOCUMENTS

| | | | |
|---|---|---|---|
| 5,795,287 A | | 8/1998 | Ball et al. |
| 5,800,336 A | | 9/1998 | Ball et al. |
| 5,857,958 A | | 1/1999 | Ball et al. |
| 6,056,735 A | * | 5/2000 | Okada ............ A61B 17/320092 606/1 |
| 6,217,508 B1 | * | 4/2001 | Ball ........................ H04R 11/02 600/25 |
| 6,408,496 B1 | | 6/2002 | Maynard |
| 2001/0031996 A1 | | 10/2001 | Leysieffer |
| 2003/0142845 A1 | * | 7/2003 | Miyamoto et al. ........... 381/396 |
| 2004/0064151 A1 | * | 4/2004 | Mollenauer ................... 606/205 |
| 2004/0243177 A1 | * | 12/2004 | Svehla ................... A61B 17/30 606/210 |
| 2005/0021078 A1 | * | 1/2005 | Vleugels et al. ............. 606/205 |
| 2005/0192612 A1 | * | 9/2005 | Houser et al. ................ 606/169 |
| 2005/0192676 A1 | * | 9/2005 | Sears ........................ A61F 2/68 623/24 |
| 2005/0267388 A1 | * | 12/2005 | Hanna .................... A61H 23/02 601/70 |
| 2006/0105691 A1 | * | 5/2006 | Schneider ..................... 452/135 |
| 2006/0200180 A1 | * | 9/2006 | Lee ............... 606/169 |
| 2007/0083078 A1 | | 4/2007 | Easter et al. |
| 2007/0225787 A1 | | 9/2007 | Simaan et al. |
| 2008/0263872 A1 | * | 10/2008 | Ferk et al. ...................... 30/228 |
| 2008/0275465 A1 | * | 11/2008 | Paul ................... A61B 18/1492 606/129 |
| 2009/0023976 A1 | | 1/2009 | Cho et al. |
| 2009/0030437 A1 | * | 1/2009 | Houser .......... A61B 17/320092 606/169 |
| 2009/0082705 A1 | * | 3/2009 | Asfora ........................... 601/46 |
| 2009/0131742 A1 | | 5/2009 | Cho et al. |
| 2010/0179457 A1 | * | 7/2010 | Blaine et al. .................. 601/46 |

FOREIGN PATENT DOCUMENTS

| | | |
|---|---|---|
| WO | 2008077943 A2 | 7/2008 |
| WO | 2010151768 A1 | 12/2010 |

* cited by examiner

Section A-A
FIG. 4B

FIG. 9

INSERTION SYSTEM FOR INSERTING IMPLANTABLE ELECTRODE CARRIER

CROSS-REFERENCE TO RELATED APPLICATIONS

The present application is a national stage application of International Application No. PCT/US2010/039996 filed Jun. 25, 2010, which claims priority to U.S. Provisional Patent Application No. 61/220,630 filed Jun. 26, 2009, the disclosures of which are incorporated by reference herein in their entirety.

FIELD OF THE INVENTION

The present invention generally relates to an insertion system for medical implants and, more particularly, the invention relates to an insertion system for implantable electrode carriers that improve the insertion process of the electrode carriers.

BACKGROUND OF THE INVENTION

For many patients with severe to profound hearing impairment, there are several types of middle-ear and inner-ear implants that can restore a sense of partial or full hearing. For example, cochlear implants can restore some sense of hearing by direct electrical stimulation of the neural tissue of the inner ear or cochlea. The cochlear implant typically includes an electrode carrier having an electrode lead and an electrode array, which is threaded into the cochlea. The electrode array usually includes multiple electrodes on its surface that electrically stimulate auditory nerve tissue with small currents delivered by the electrodes distributed along the electrode array. These electrodes are typically located toward the end of the electrode carrier and are in electrical communication with an electronics module that produces an electrical stimulation signal for the implanted electrodes to stimulate the cochlea.

One of the important steps in cochlear implant surgery is the insertion of the electrode array into the scala tympani of the cochlea. In some cases, this insertion process can be disrupted when the continuous movement of the electrode carrier into the cochlea gets disturbed due to increased frictional forces between the cochlea wall and the electrode array, or due to small obstacles preventing the electrode carrier from smoothly moving along the insertion path. In both cases, the electrode carrier may become damaged if it is excessively bent when being pushed further inside the cochlea while the tip or other parts of the electrode carrier are prevented from moving forward. Furthermore, x-ray microscopy studies by Hüttenbrink et al. allowed a visualization of the frictional behaviour of electrodes in the inner ear and revealed that in some cases there might be the danger of kinking of the electrode carrier inside of the scala tympani. A subsequent contact pressure between electrode and basilar membrane which may lead to rupture of the basilar membrane is very likely to damage anatomical structures of the inner ear and destroy residual hearing. Such damage is not acceptable with the latest trends in Electric Acoustic Stimulation (EAS) technology and cochlear implant surgery to preserve any residual hearing.

To minimize these problems, lubricating substances are sometimes used on the electrode carrier to reduce the frictional forces between electrode carrier and the cochlea. However, it is questionable whether these lubricating substances are able to prevent typically occurring problems during the insertion process and currently have not become a commonly accepted clinical practice.

Another issue which is observed in cochlear implant surgery is the floppiness of the electrode carrier in the mastoidectomy and posterior tympanatomy which may make it difficult to guide the electrode carrier to the cochleostomy or round window without picking up blood or other fluids from the surrounding tissues. A contamination of the electrode carrier with blood represents another potential hazard to the residual hearing of patients.

U.S. Patent Application Publication No. 2007/0225787 to Simaan et. al. ("Simaan") teaches active-bending electrodes and corresponding insertion systems for inserting same. In this context, an electrode applicator is mentioned which reduces the frictional forces as the electrode traverses the inner ear by applying vibrations to the electrode array. However, the insertion systems disclosed therein include a controller located remotely, making the systems bigger and more unwieldy. In addition, Simaan fails to provide any teachings on how, and by what mechanism, the insertion system generates the vibrations in the electrode array.

SUMMARY OF THE INVENTION

In accordance with one embodiment of the invention, an insertion system for inserting an implantable electrode carrier includes a housing having a proximal end and a distal end, and a vibration generator coupled adjacent to the housing. The proximal end is configured to hold the implantable electrode carrier, and the vibration generator is configured to generate vibrations in at least a portion of the electrode carrier.

In related embodiments, the vibration generator may be adjacent to the proximal end of the housing, the distal end of the housing, or between the proximal end and the distal end of the housing. The system may further include a power supply coupled to the vibration generator and positioned within the housing. The power supply is configured to supply energy to the vibration generator. The vibration generator may include a floating mass transducer. The floating mass transducer may include a bushing having an inner area, a permanent magnet positioned within the inner area of the bushing, and an electromagnetic coil adjacent to a portion of the bushing. The electromagnetic coil is configured to move the permanent magnet within the inner area of the bushing. The floating mass transducer may further include at least one spring positioned between the permanent magnet and one end of the bushing so that the at least one spring is configured to move the permanent magnet back to a neutral position after the electromagnetic coil moves the permanent magnet within the inner area of the bushing. The permanent magnet may be cylindrical or spherical in shape.

The vibration generator may include an electromotor connected to a gear, and a mass connected to the gear. The mass is configured to produce at least a portion of the vibrations generated by the vibration generator when the gear moves the mass. The vibration generator may include an electromotor connected to a gear having an unbalanced mass. The unbalanced mass is configured to produce at least a portion of the vibrations generated by the vibration generator when the gear moves the unbalanced mass. The system may further include one or more sensors positioned near the distal end of the housing. The one or more sensors are configured to sense a force applied to the system, and the vibration generator is configured to control vibration parameters based on the sensed force. The vibration generator may impart longitudinal oscillations, transverse oscillations, rotational oscillations, or a combination thereof, to the proximal end of the housing. The vibration generator may include a piezoelectric actuator, a pneumatic actuator, an hydraulic actuator, an electrodynamic actuator and/or a mechanical actuator.

In accordance with another embodiment of the invention, an insertion system for inserting an implantable electrode carrier includes a housing having a coupling mechanism configured to secure the housing to the implantable electrode carrier, and a vibration generator positioned within the housing. The vibration generator is configured to generate vibrations in at least a portion of the electrode.

In related embodiments, the system may further include an insertion instrument having a proximal end and a distal end. The proximal end is configured to hold the implantable electrode carrier during insertion. The system may further include one or more sensors in the insertion instrument near its distal end. The one or more sensors are configured to sense a force applied to the instrument, and the vibration generator is configured to control vibration parameters based on the sensed force. The system may further include a power supply coupled to the vibration generator. The power supply is configured to supply energy to the vibration generator. The power supply may be positioned within the housing.

The vibration generator may include a floating mass transducer. The floating mass transducer may include a bushing having an inner area, a permanent magnet positioned within the inner area of the bushing, and an electromagnetic coil adjacent to a portion of the bushing. The electromagnetic coil is configured to move the permanent magnet within the inner area of the bushing. The floating mass transducer may further include at least one spring positioned between the permanent magnet and one end of the bushing so that the at least one spring is configured to move the permanent magnet back to a neutral position after the electromagnetic coil moves the permanent magnet within the inner area of the bushing. The permanent magnet may be cylindrical or spherical in shape. The vibration generator may include an electromotor connected to a gear, and a mass connected to the gear. The mass is configured to produce at least a portion of the vibrations generated by the vibration generator when the gear moves the mass. The vibration generator may include an electromotor connected to a gear having an unbalanced mass. The unbalanced mass is configured to produce at least a portion of the vibrations generated by the vibration generator when the gear moves the unbalanced mass. The vibration generator may be configured to impart longitudinal oscillations, transverse oscillations and/or rotational oscillations to the implantable electrode carrier. The vibration generator may include a piezoelectric actuator, a pneumatic actuator, an hydraulic actuator, an electrodynamic actuator and/or a mechanical actuator.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Various embodiments of the present invention provide an insertion system for inserting an implantable electrode carrier, and methods of inserting the electrode carrier, that improves the current implantation process for electrodes. The insertion system includes an insertion instrument having a housing with a proximal end and a distal end, and a vibration generator which is coupled adjacent to the housing. The proximal end is configured to hold the implantable electrode carrier, and the vibration generator is configured to generate vibrations in at least a portion of the electrode carrier. Alternatively, the insertion system includes a housing having a coupling mechanism configured to secure the housing to the implantable electrode carrier, and a vibration generator positioned within the housing. Details of illustrative embodiments are discussed below.

Figure 1:
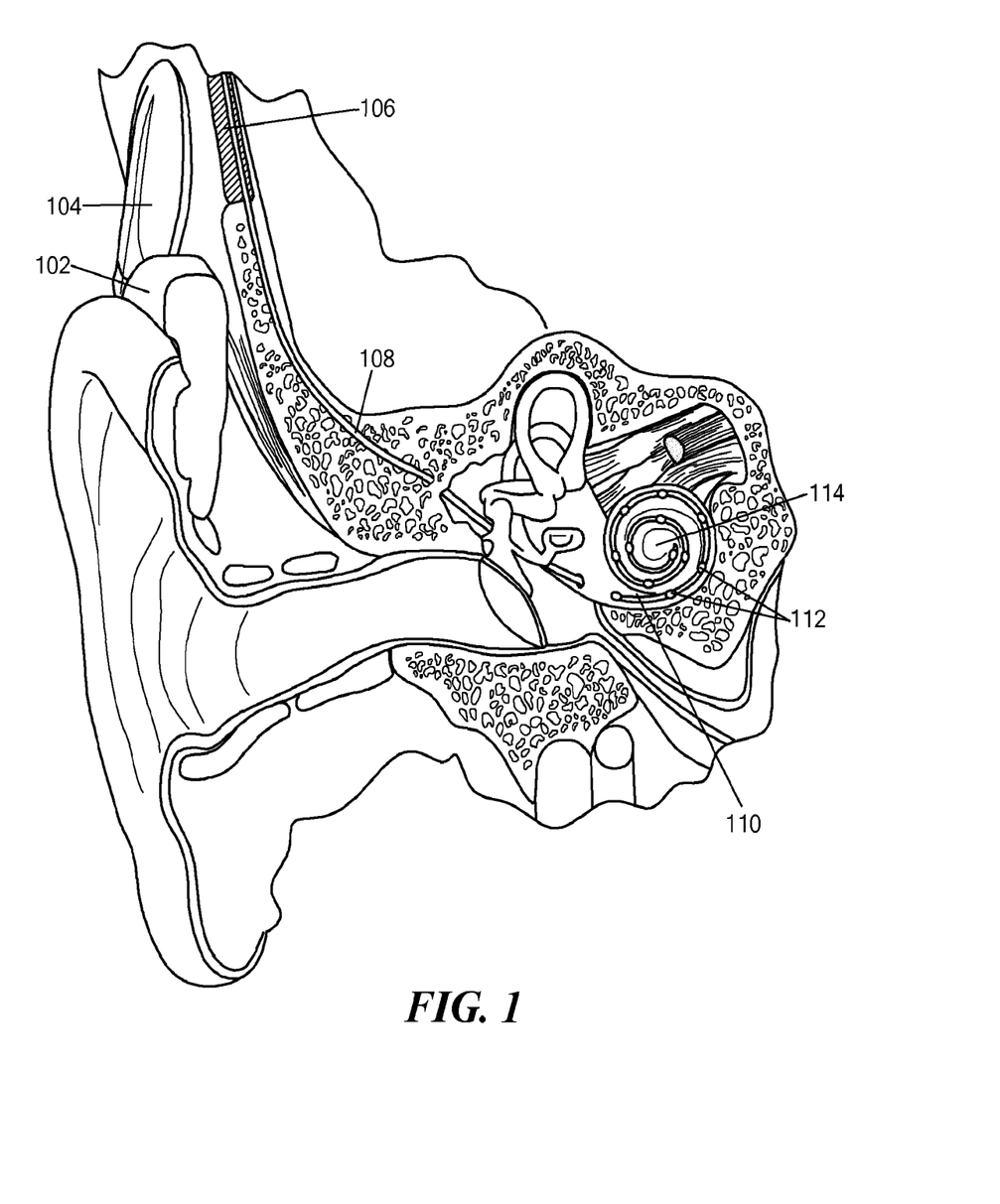
FIG. 1 schematically shows a typical human ear which includes a cochlear implant system.

FIG. 1 schematically shows the anatomy of a normal human ear and some components of a typical cochlear implant system. As shown, the cochlear implant system includes an external microphone (not shown) that provides an audio signal input to an external signal processor 102 where various signal processing schemes may be implemented. The processed signal is then converted into a stimulation pattern by an external transmitter/stimulator 104, and the stimulation pattern/signal is transmitted through connected wires (not shown) to an implanted electrode carrier 106. The electrode carrier 106 has an electrode lead 108 and an electrode array 110. Typically, the electrode array 110 has multiple electrodes 112 on its surface that provide selective stimulation to the cochlea 114.

Figure 2:
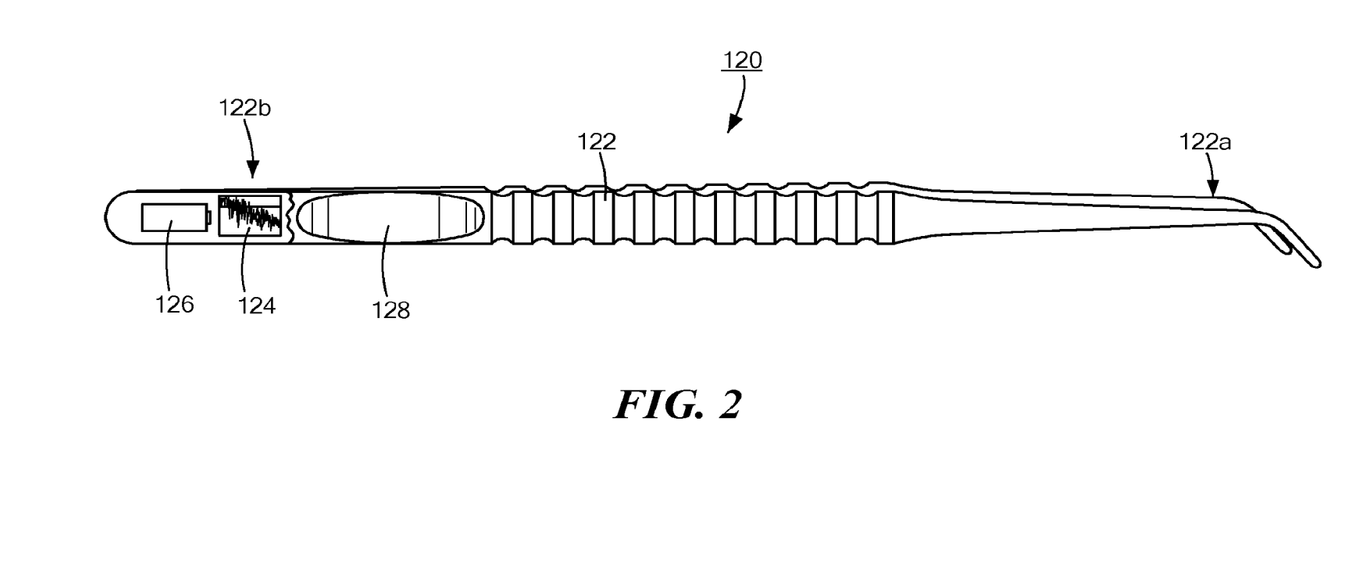
FIG. 2 schematically shows an exemplary insertion instrument with an integrated vibration generator according to embodiments of the present invention.

FIG. 2 schematically shows an illustrative embodiment of an insertion instrument 120 with an integrated vibration generator that may be used to implant an electrode carrier. The instrument 120 includes a housing 122 having a proximal end 122a and a distal end 122b. The proximal end 122a is configured to hold the implantable electrode carrier (not shown in FIG. 2). The instrument 120 also includes a vibration generator 124 positioned within the housing 122, in the distal end 122b and/or proximal end 122a of the housing. The vibration generator 124 is configured to generate vibrations in at least a portion of the electrode carrier. The housing 122 has a longitudinal axis from the proximal end 122a to the distal end 122b of the housing, and the vibration generator may be concentric to the longitudinal axis or offset from this axis. For example, the vibration generator 124 may be coupled or adjacent to an inner surface of the housing in one or more locations so that the vibration generator 124 is relatively equally spaced from the sides of the housing. Alternatively, the vibration generator 124 may be coupled or adjacent to one portion of the inner surface of the housing so that the vibration generator 124 is closer to one side of the housing than the other, offset from the center, longitudinal axis. The vibration generator 124 will be described in more detail below.

Embodiments of the instrument 120 may also include a power supply 126 positioned within the housing 122 and coupled to the vibration generator 124. Preferably, the power supply 126 is positioned within the distal end of the housing 122. The power supply 126 supplies energy to the vibration generator 124. The instrument 120 may include a standard instrument handle 128 at the distal end of the housing 122 which allows a surgeon to grip the instrument, guide it and the cochlear implant electrode carrier to the cochleostomy, and insert the electrode array into the cochlea. Although one configuration of the instrument 120 is shown, any standard instrument geometry may be used, e.g., forceps, tweezers, or surgical claws, that allows an integrated vibration generator 124.

Embodiments of the instrument 120 may also include one or more sensors (not shown) positioned on or in the housing 122. The sensor(s) may be used to detect a force which is applied to the instrument 120, and the sensed force may be used as an input for the vibration generator 124. The sensor(s) may be used to give surgeons the ability to control various vibration parameters generated by the vibration generator 124 (e.g., an increased pressure on the handle of the instrument by the surgeon may increase the amplitude and/or frequency of the vibrations). This may allow surgeons to implement the instrument and its vibrations in a much more controlled way. A stopper (not shown) may also be used with the instrument 120 to prevent overloading of the electrode carrier caused by any high closing forces of the instrument 120.

Embodiments of the vibration generator 124 are configured to couple vibrations to at least a portion of the electrode carrier. The frequency and amplitude of the vibrations produced by the vibration generator 124 are preferably chosen such that the oscillations produced in the electrode carrier help to overcome the friction effects and obstacles encountered when inserting the electrode carrier into the cochlea, reducing possible insertion trauma. In addition, or alternatively, the vibrations may be adapted to the vibration characteristics of one or more portions of the electrode carrier such that any large amplitude deflections of the electrode carrier may be suppressed or substantially suppressed. The instrument 120 may have one or more different vibration modes to provide optimal behaviour of the electrode carrier inside and outside the cochlea. The vibration parameters may be optimized to improve the electrode carrier movement, to improve the stability of the electrode carrier (e.g., to avoid transversal oscillations of a floppy electrode carrier), and/or to improve the smoothness of the electrode carrier insertion process. Vibration parameters may include amplitude, frequency, ascending and descending slope of the vibration signal and its waveform in general. Modes of vibrations may include sinusoidal, triangular, square-wave, saw-tooth-like signals or a combination of two or more of these modes.

Various types of systems may be used for the vibration generator 124. For example, the vibration generator 124 may include electrodynamic actuators, piezoelectric actuators, pneumatic actuators, hydraulic actuators, and/or mechanical gear systems, although other systems may also be used. Preferably, the frequency of the vibrations may range between 0 to about 100 kHz and the amplitude of the vibrations may range between 0 to about 5 mm Longitudinal, transverse and/or rotational oscillations may be applied by the vibration generator 124 to the electrode carrier depending on the configuration of the vibration generator 124.

Figure 3:
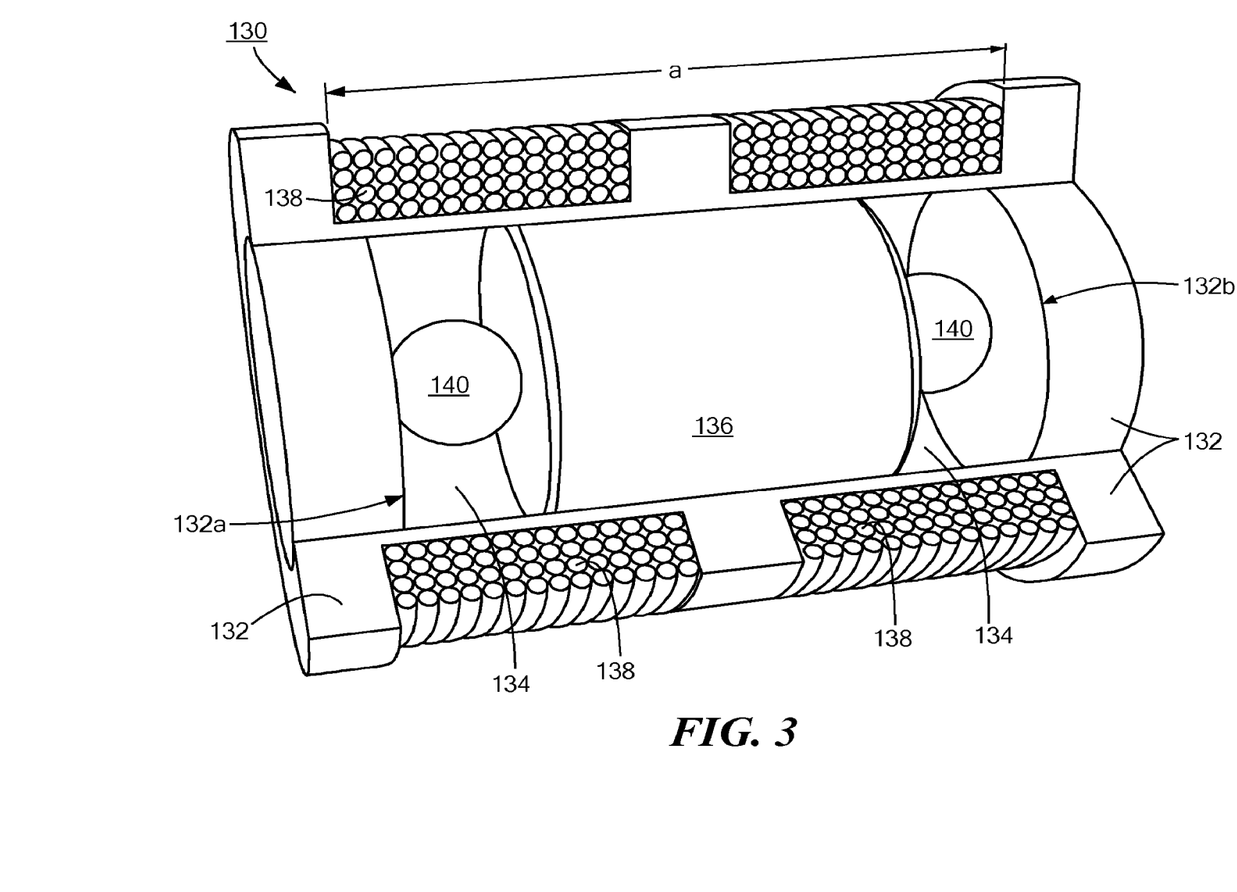
FIG. 3 schematically shows an electrodynamic vibration generator that permits axial vibrations according to embodiments of the present invention.

For example, FIG. 3 schematically shows an exemplary floating mass transducer 130 that may be used as a vibration generator 124 to generate longitudinal or transverse oscillations within the electrode carrier 106 depending on the orientation of the transducer 130 in the instrument 120. As shown, the floating mass transducer 130 includes a bushing 132 having an inner area 134 and a permanent magnet 136 positioned within the inner area 134. Preferably, the permanent magnet is cylindrical (shown) or spherical (not shown) in shape. The bushing 132 allows the permanent magnet 136 to move within the inner area 134 toward either end 132a, 132b of the bushing 132, and generally along axis, a, as shown. The floating mass transducer 130 further includes at least one electromagnetic coil 138 adjacent to a portion of the bushing 132. As known by those skilled in the art, a current may be passed through the electromagnetic coil 138, which creates a magnetic field within the inner area 134 of the bushing 132. In response to this magnetic field, the permanent magnet 136 moves within the inner area 134 of the bushing 132 either toward end 132a or end 132b, depending on the direction of the magnetic field. As known by those skilled in the art, the direction of the magnetic field may be changed depending on the direction of the current flow within the electromagnetic coil 138. The movement of the permanent magnet 136 within the inner area 134 of the bushing 132 causes vibrations to be produced by the floating mass transducer 130.

The floating mass transducer 130 may optionally include one or more springs or dampers 140 positioned between the permanent magnet 136 and either end 132a, 132b of the bushing 132. After the electromagnetic coil 138 has moved the permanent magnet 136 within the inner area 134, the spring(s) 140 may provide a restoring force to the permanent magnet 136 and move the permanent magnet 136 back to a neutral position within the inner area 134. The bushing 132 may be hermetically sealed so as to prevent corrosion and/or leakage of material into or out of the bushing 132. Preferably, the bushing 132 is made of a non-ferromagnetic material and may be made of a biocompatible material, e.g., stainless steel, titanium, aluminum, platinum, nylon and/or a ceramic material.

Figure 4A:
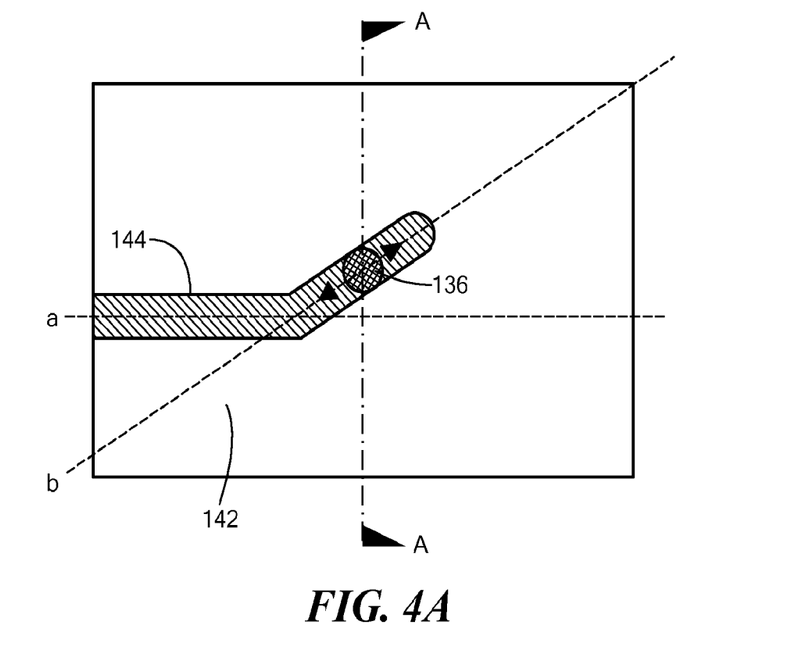
FIGS. 4A and 4B schematically show a bushing for an electrodynamic vibration generator that permits axial and torsional vibrations according to embodiments of the present invention.
Figure 4B:
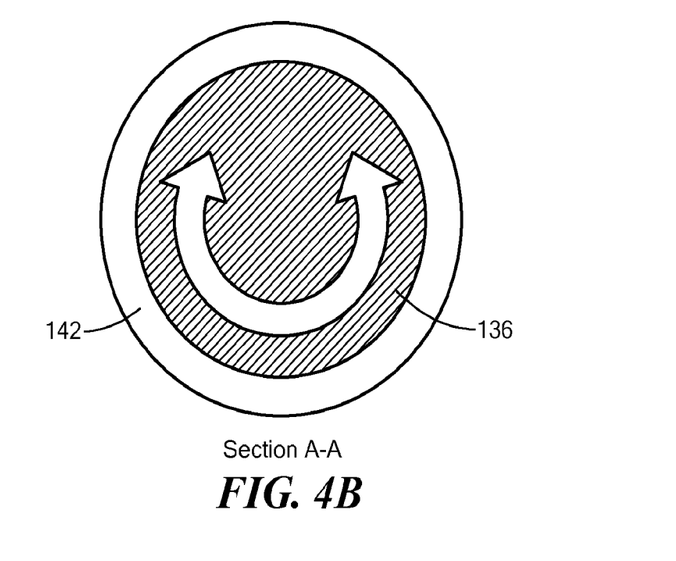

Although FIG. 3 shows a floating mass transducer 130 that generates axial vibrations, the configuration of the inner area 134 within the bushing 132 may be modified to permit axial and torsional vibrations according to embodiments of the present invention. For example, FIG. 4A schematically shows a longitudinal cross-section of a bushing 142 and its inner area 144, and FIG. 4B schematically shows a transverse cross-sectional view along line A-A of FIG. 4A that may be used within a floating mass transducer to generate both axial and torsional vibrations. As shown, the permanent magnet 136 may move generally along axis a and axis b (shown as dashed lines in FIG. 4A) as well as rotate or turn within the inner area 144. An advantage of adding rotational vibrations to translational rotation is that rotational vibrations may be especially effective when trying to overcome obstacles during electrode carrier insertion.

Figure 5:
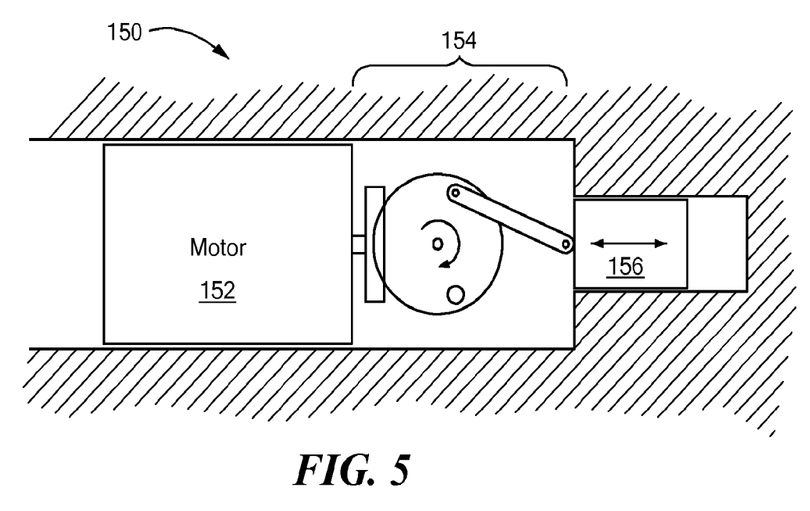
FIG. 5 schematically shows an electromotor vibration generator that permits multidimensional vibrations according to embodiments of the present invention.
Figure 6A:
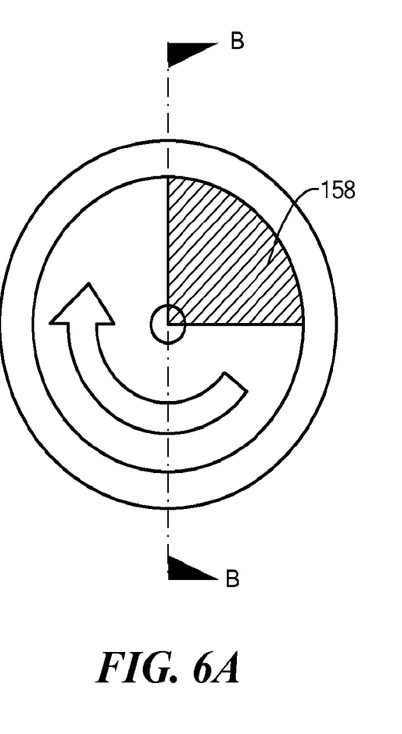
FIG. 6A schematically shows one portion of a gear with an unbalanced mass that permits multidimensional vibrations according to embodiments of the present invention.
Figure 6B:
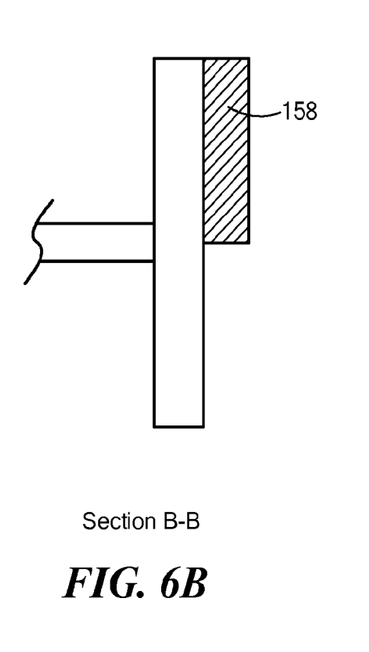
FIG. 6B schematically shows a cross-sectional view along lines B-B of FIG. 6A.

Another configuration of a vibration generator 124 that may be used is a miniaturized electromotor. For example, FIG. 5 schematically shows an electromotor 150 that permits multidimensional vibrations according to embodiments of the present invention. As shown, the electromotor 150 may include a motor 152 connected to a gear 154, which in turn is connected to a mass 156 that may move back and forth generally in the direction shown with arrows. As shown in FIGS. 6A and 6B, the gear 154 may have an unbalanced mass 158, which when the gear rotates, may generate multidimensional vibrations. An advantage of a mechanical gear solution is that the individual parts are generally inexpensive, simple and reliable.

An advantage of positioning the vibration generator 124 within the instrument housing 122 is that the entire vibration unit, including vibration generator 124, power supply 126 and any electronics, is very compact and may be completely detached from the instrument housing 122 for sterilization of the housing 122.

Figure 7:
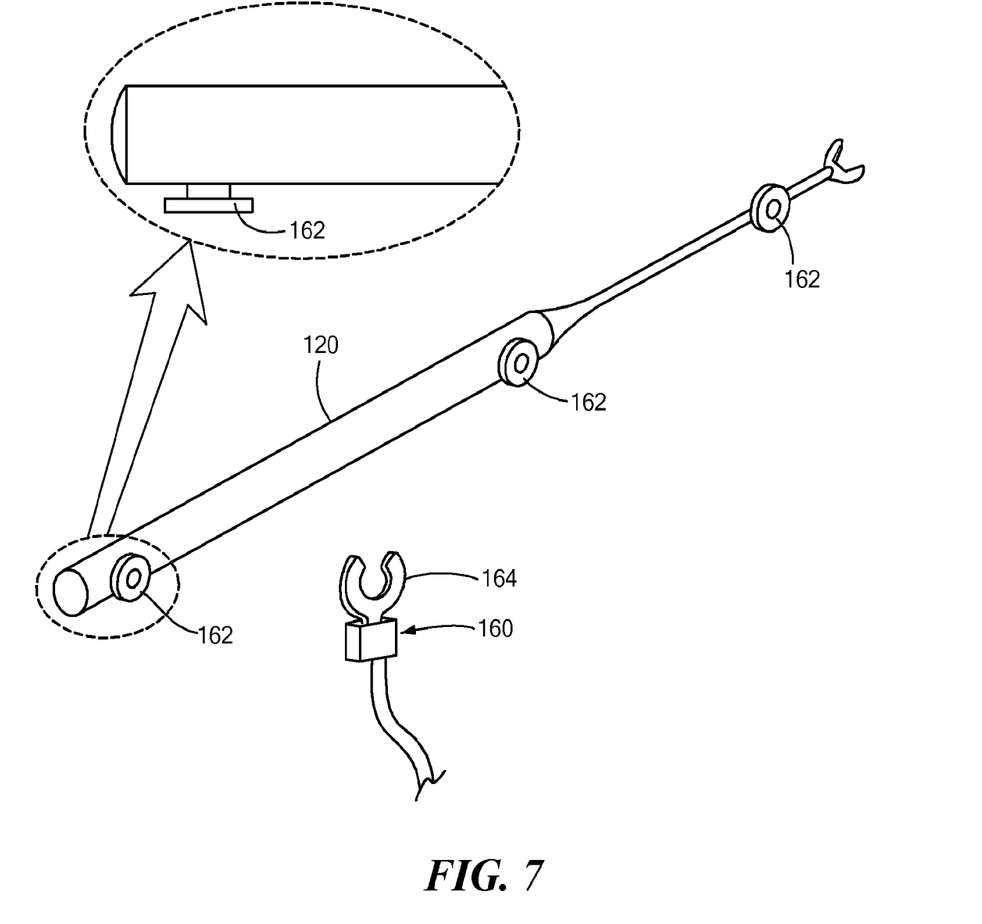
FIG. 7 schematically shows a vibration generator coupled adjacent to an insertion instrument according to embodiments of the present invention.

Although an insertion system having an insertion instrument with an integral vibration generator is discussed above, other configurations may also be used in order to transmit vibrations to the electrode carrier via the instrument. FIG. 7 schematically shows an insertion system with a vibration generator 124 coupled adjacent to the insertion instrument 120 on the outside of the instrument housing 122. In this case, the vibration generator 124 is positioned within a vibration generator housing 160 that is directly attached to the instrument 120 at one or more coupling points 162 using a coupling mechanism 164. The coupling mechanism 164 that connects the vibration generator housing 160 to the instrument 120 may be any system that allows the vibrations to be directly transmitted from the vibration generator housing 160 to the instrument 120, e.g., a screw connection, a clamping mechanism (e.g., clamping screw) and/or a form-fit mechanism (e.g., bayonet lock). The coupling points 162 may be in the distal end 122b of the instrument 120, the proximal end 122a of the instrument 120, and/or between the distal and proximal ends. The power supply 126 for the vibration generator 124 may be included within the generator housing 160 or the insertion instrument housing 122, or may be located externally from either of the housings 122, 160, but electrically coupled to vibration generator 124. Embodiments with an externally coupled vibration generator 124 may provide more vibration energy than having the vibration generator 124 positioned within the housing 122 of the instrument 120.

Figure 8:
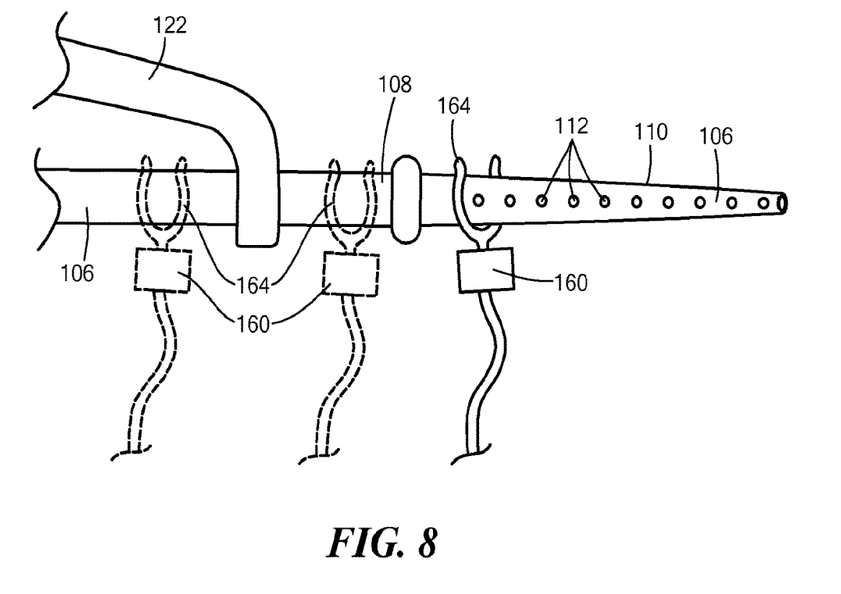
FIG. 8 schematically shows a vibration generator coupled adjacent to an electrode carrier according to embodiments of the present invention.

Rather than having the vibration generator 124 coupled adjacent to the insertion instrument 120, other embodiments may include the vibration generator 124 coupled adjacent to the electrode carrier 106 itself, such as shown in FIG. 8. In this case, vibration generator housing 160 includes a coupling mechanism 164 configured to secure the vibration generator housing 160 to the electrode carrier 106. The vibration generator housing 160 may be secured to the electrode carrier 106 anywhere along its length, e.g., near the electrode array 110 and/or the electrode lead 108. The proximal end of the insertion instrument 122 is then configured to hold the electrode carrier 106 along with the vibration generator 124 within the vibration generator housing 160.

Figure 9:
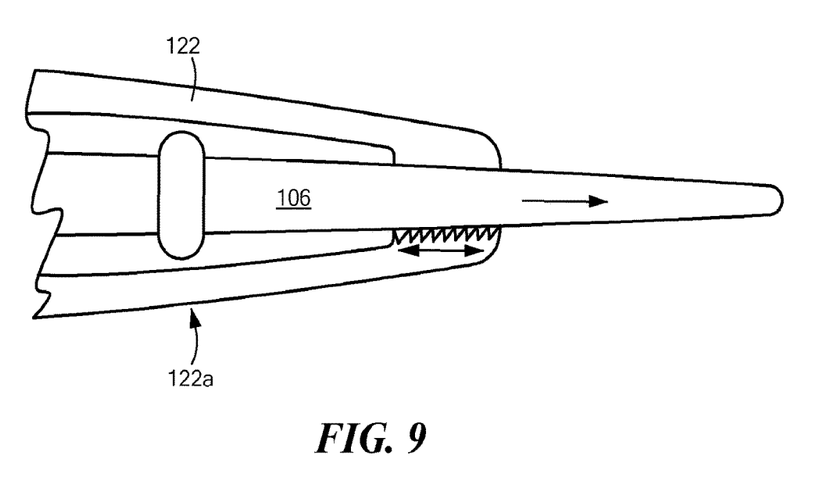
FIG. 9 schematically shows a portion of an instrument holding an implantable electrode carrier according to embodiments of the present invention.

Some embodiments may provide improved methods of inserting the electrode carrier into the cochlea. For example, as shown in FIG. 9, the system may be configured so that the vibrations generated impart an axial motion to the instrument housing 122 (as shown by the double-sided arrow), which may cause the electrode carrier 106 to move forward (as shown by the arrow) with a constant, incremental movement. In embodiments where the vibration generator 124 is coupled adjacent to the electrode carrier 106, the vibrations generated may be imparted directly to the electrode carrier rather than through the instrument housing 122. In either case, this may produce an adjustable feed rate of the electrode carrier 106 into the cochlea which may result in a constant, slow and atraumatic insertion process. This automated insertion method may eliminate the need to have the surgeon repeatedly grip the electrode carrier 106 with the instrument 120 or apply mechanical force to the electrode carrier 106. This approach may further reduce the trauma associated with implanting the electrode carrier 106 into the cochlea since the constant, slow insertion process may automatically choose the path of lowest resistance. The insertion system may also be configured with a mode which allows moving the electrode carrier 106 in the reverse direction, reducing the forces occurring during explantation of electrode carriers 106.

Accordingly, various embodiments of the present invention improve the electrode insertion process by applying vibrations to the electrode carrier. Embodiments should not produce any negative effects on hearing preservation since the motions which are introduced by the vibrations are negligible in comparison to the overall electrode insertion trauma.

Although the above discussion discloses various exemplary embodiments of the invention, it should be apparent that those skilled in the art can make various modifications that will achieve some of the advantages of the invention without departing from the true scope of the invention.

What is claimed is:

1. An insertion system for inserting an implantable electrode carrier into an inner ear, the system comprising:
   an insertion instrument having a housing with a proximal end and a distal end, the proximal end having movable, opposing members configured to move relative to one another in only a closing and unclosing direction and configured to releasably hold the implantable electrode carrier, and the distal end having a handle configured to allow a surgeon to grip the instrument and one or more sensors positioned on or in the housing, the one or more sensors configured to sense a force applied to the handle;
   a vibration generator coupled adjacent to an inner surface or an outer surface of the housing, the vibration generator configured to generate vibrations in at least a portion of the housing, configured to transmit the vibrations to the electrode carrier via the insertion instrument, and configured to control vibration parameters when the vibrations are generated based on the sensed force in order to vary the vibrations generated in the proximal end so as to cause vibrations in the electrode carrier during an insertion process; and
   a power supply positioned within the housing, the power supply configured to supply energy to the vibration generator.

2. The system of claim 1, wherein the vibration generator is adjacent to the proximal end of the housing, the distal end of the housing, or between the proximal end and the distal end of the housing.

3. The system of claim 1, wherein the power supply is coupled to the vibration generator.

4. The system of claim 1, wherein the vibration generator imparts longitudinal oscillations, transverse oscillations, rotational oscillations, or a combination thereof, to the proximal end of the housing.

5. The system of claim 1, wherein the vibration generator includes a pneumatic actuator, an hydraulic actuator, an electrodynamic actuator, a mechanical actuator, or a combination thereof.

6. The system of claim 1, wherein the vibration generator is adjacent to the inner surface of the housing and positioned within the housing.

7. The system of claim 6, wherein the vibration generator is positioned within the distal end of the housing, the proximal end of the housing, or both.

8. The system of claim 1, wherein the vibration parameters include frequency, amplitude, ascending slope of a vibration signal, descending slope of the vibration signal, a wave form of the vibration signal, or combinations thereof.

9. The system of claim 1, wherein the vibration generator includes two or more different vibration modes to provide the vibration parameters, wherein the vibration modes include sinusoidal, triangular, square-wave, saw-tooth-like vibration signals or combinations thereof.

10. The system of claim 1, wherein the vibration generator includes a floating mass transducer.

11. The system of claim 10, wherein the floating mass transducer comprises:
a bushing having an inner area;
a permanent magnet positioned within the inner area of the bushing; and
an electromagnetic coil adjacent to a portion of the bushing, the electromagnetic coil configured to move the permanent magnet within the inner area of the bushing.

12. The system of claim 11, wherein the floating mass transducer further includes at least one spring positioned between the permanent magnet and one end of the bushing so that the at least one spring is configured to move the permanent magnet back to a neutral position after the electromagnetic coil moves the permanent magnet within the inner area of the bushing.

13. The system of claim 11, wherein the permanent magnet is cylindrical or spherical in shape.

14. The system of claim 1, wherein the vibration generator includes an electromotor connected to a gear.

15. The system of claim 14, wherein the vibration generator includes a mass connected to the gear, wherein the mass is configured to produce at least a portion of the vibrations generated by the vibration generator when the gear moves the mass.

16. The system of claim 14, wherein the vibration generator includes an unbalanced mass connected to the gear, wherein the unbalanced mass is configured to produce at least a portion of the vibrations generated by the vibration generator when the gear moves the unbalanced mass.

17. An insertion system for inserting an implantable electrode carrier into an inner ear, the system comprising:
an insertion instrument having a proximal end and a distal end, the proximal end having movable, opposing members configured to move relative to one another in only a closing and unclosing direction and configured to releasably hold the implantable electrode carrier during insertion, and the distal end having a handle configured to allow a surgeon to grip the insertion instrument and one or more sensors positioned on or in the instrument, the one or more sensors configured to sense a force applied to the handle;
a housing having a coupling mechanism configured to secure the housing to the implantable electrode carrier;
a vibration generator positioned within the housing, the vibration generator configured to generate vibrations in at least a portion of the housing, configured to transmit the vibrations to the electrode carrier via the insertion instrument, and configured to control vibration parameters when the vibrations are generated based on the sensed force in order to vary the vibrations generated in the proximal end so as to cause vibrations in the electrode carrier during an insertion process; and
a power supply coupled to the vibration generator and positioned within the housing, the power supply configured to supply energy to the vibration generator.

18. The system of claim 17, wherein the vibration generator is configured to impart longitudinal oscillations, transverse oscillations, rotational oscillations, or a combination thereof, to the implantable electrode carrier.

19. The system of claim 17, wherein the vibration generator includes a pneumatic actuator, an hydraulic actuator, an electrodynamic actuator, a mechanical actuator, or a combination thereof.

20. The system of claim 17, wherein the vibration parameters include frequency, amplitude, ascending slope of a vibration signal, descending slope of the vibration signal, a wave form of the vibration signal or combinations thereof.

21. The system of claim 17, wherein the vibration generator includes a floating mass transducer.

22. The system of claim 21, wherein the floating mass transducer comprises:
a bushing having an inner area;
a permanent magnet positioned within the inner area of the bushing; and
an electromagnetic coil adjacent to a portion of the bushing, the electromagnetic coil configured to move the permanent magnet within the inner area of the bushing.

23. The system of claim 22, wherein the floating mass transducer further includes at least one spring positioned between the permanent magnet and one end of the bushing so that the at least one spring is configured to move the permanent magnet back to a neutral position after the electromagnetic coil moves the permanent magnet within the inner area of the bushing.

24. The system of claim 22, wherein the permanent magnet is cylindrical or spherical in shape.

25. The system of claim 17, wherein the vibration generator includes an electromotor connected to a gear.

26. The system of claim 25, wherein the vibration generator includes an unbalanced mass connected to the gear, wherein the unbalanced mass is configured to produce at least a portion of the vibrations generated by the vibration generator when the gear moves the unbalanced mass.

27. An insertion system for inserting an implantable electrode carrier, the system comprising:
an insertion instrument having a housing with a proximal end and a distal end, the proximal end having movable, opposing members configured to releasably hold the implantable electrode carrier and the distal end having a handle configured to allow a surgeon to grip the instrument and one or more sensors positioned on or in the housing, the one or more sensors configured to sense a force applied to the handle;

a vibration generator coupled adjacent to an inner surface or an outer surface of the housing, the vibration generator configured to generate vibrations in at least a portion of the housing and configured to transmit the vibrations to the electrode carrier via the insertion instrument, and configured to control vibration parameters when the vibrations are generated based on the sensed force in order to vary the vibrations generated in the proximal end so as to cause vibrations in the electrode carrier during an insertion process, wherein the vibration generator includes a floating mass transducer; and a power supply positioned within the housing, the power supply configured to supply energy to the vibration generator.

28. The system of claim 27, wherein the floating mass transducer comprises:

a bushing having an inner area;

a permanent magnet positioned within the inner area of the bushing; and an electromagnetic coil adjacent to a portion of the bushing, the electromagnetic coil configured to move the permanent magnet within the inner area of the bushing.

29. The system of claim 28, wherein the floating mass transducer further includes at least one spring positioned between the permanent magnet and one end of the bushing so that the at least one spring is configured to move the permanent magnet back to a neutral position after the electromagnetic coil moves the permanent magnet within the inner area of the bushing.

30. The system of claim 28, wherein the permanent magnet is cylindrical or spherical in shape.

31. An insertion system for inserting an implantable electrode carrier, the system comprising:

an insertion instrument having a proximal end and a distal end, the proximal end having movable, opposing members configured to releasably hold the implantable electrode carrier during insertion and the distal end having a handle configured to allow a surgeon to grip the insertion instrument and one or more sensors positioned on or in the instrument, the one or more sensors configured to sense a force applied to the handle;

a housing having a coupling mechanism configured to secure the housing to the implantable electrode carrier;

a vibration generator positioned within the housing, the vibration generator configured to generate vibrations in at least a portion of the housing and configured to transmit the vibrations to the electrode carrier via the insertion instrument, and configured to control vibration parameters when the vibrations are generated based on the sensed force in order to vary the vibrations generated in the proximal end so as to cause vibrations in the electrode carrier during an insertion process, wherein the vibration generator includes a floating mass transducer; and a power supply coupled to the vibration generator and positioned within the housing, the power supply configured to supply energy to the vibration generator.

32. The system of claim 31, wherein the floating mass transducer comprises:

a bushing having an inner area;

a permanent magnet positioned within the inner area of the bushing; and an electromagnetic coil adjacent to a portion of the bushing, the electromagnetic coil configured to move the permanent magnet within the inner area of the bushing.

33. The system of claim 32, wherein the floating mass transducer further includes at least one spring positioned between the permanent magnet and one end of the bushing so that the at least one spring is configured to move the permanent magnet back to a neutral position after the electromagnetic coil moves the permanent magnet within the inner area of the bushing.

34. The system of claim 32, wherein the permanent magnet is cylindrical or spherical in shape.

\* \* \* \* \*